Figure 1:
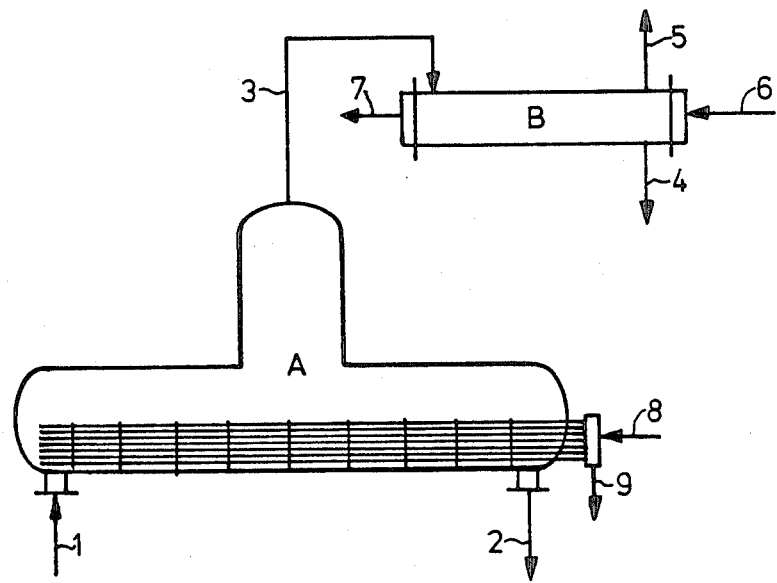

United States Patent [19]

Lailach et al.

[11] Patent Number: 4,772,757
[45] Date of Patent: Sep. 20, 1988

[54] PROCESS FOR THE PRODUCTION OF NITROBENZENE

[75] Inventors: Günter Lailach; Rudolf Gerken; Karl-Heinz Schultz; Rudolf Hornung; Walter Böckmann; Wolfgang Larbig; Wolfgang Dietz, all of Krefeld, Fed. Rep. of Germany

[73] Assignee: Bayer Aktiengesellschaft, Leverkusen, Fed. Rep. of Germany

[21] Appl. No.: 921,641

[22] Filed: Oct. 21, 1986

Related U.S. Application Data

[63] Continuation of Ser. No. 711,903, Mar. 14, 1985, abandoned.

[30] Foreign Application Priority Data

Mar. 16, 1984 [DE] Fed. Rep. of Germany ....... 3409717

[51] Int. Cl.$^4$ .............................................. C07C 79/10
[52] U.S. Cl. .................................................... 568/939
[58] Field of Search ............................... 568/939, 934

[56] References Cited

U.S. PATENT DOCUMENTS

| | | | |
|---|---|---|---|
| 2,256,999 | 9/1941 | Castner | 568/937 |
| 3,928,475 | 12/1975 | Dassel | 568/939 |
| 4,021,498 | 5/1977 | Alexanderson et al. | 568/939 |
| 4,064,147 | 12/1977 | Thelen et al. | 568/939 |
| 4,091,042 | 5/1978 | Alexanderson et al. | 568/939 |
| 4,274,910 | 6/1981 | Forter et al. | 203/86 |
| 4,367,347 | 1/1983 | Sawicki | 568/934 |
| 4,496,782 | 1/1985 | Carr | 568/939 |

FOREIGN PATENT DOCUMENTS

1152285 8/1983 Canada .
1156428 11/1983 Canada .

*Primary Examiner*—Edward A. Miller
*Attorney, Agent, or Firm*—Sprung Horn Kramer & Woods

[57] ABSTRACT

In the production of nitrobenzene by subjecting benzene to nitration with a mixture of nitric acid and sulfuric acid, separating off the nitrobenzene formed, concentrating the sulfuric acid by evaporation and returning the concentrated sulfuric acid to the bezene nitration stage, the improvement which comprises concentrating sulfuric acid to a concentration of from 75 to 92% by evaporation in vacuo at temperatures in the range from 130° to 195° C. Thereby the energy per kg of water evaporated is drastically reduced compared to processes wherein the sulfuric acid is concentrated to a higher level, without a corresponding loss in efficiency or capacity.

16 Claims, 2 Drawing Sheets

PROCESS FOR THE PRODUCTION OF NITROBENZENE

This is a continuation of application Ser. No. 711,903, filed Mar. 14, 1985, now abandoned.

This invention relates to a process for the production of nitribenzene by subjecting benzene to isothermal nitration with a mixture of nitric acid and sulfuric acid, separating off the nitrobenzene formed, concentrating the sulfuric acid by evaporation and returning the concentrated sulfuric acid to the benzene nitration stage.

Nitrobenzene is produced by the nitration of benzene using so-called nitrating acid which is a mixture of nitric acid and sulfuric acid:

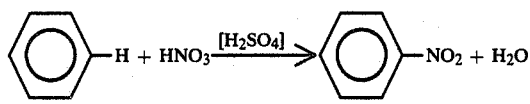

The sulfuric acid absorbs the water of reaction formed in this process. A relatively dilute sulfuric acid is formed from the nitrating acid through the water continuously formed and the consumption of nitric acid in the above reaction. In order to maintain the required working concentration, therefore, dilute acid, so-called spent acid, has to be removed from the system and replaced by concentrated acid. This represents a significant cost factor in the production process. In addition, considerable problems are presented by the presence of the spend acid which is contaminated by organic compounds and oxides of nitrogen. The use of the spent acid in the fertilizer industry presupposes appropriate measures to meet the requirements which the purity of the dilute acid has to satisfy (U.S. Pat. No. 4,257,986).

One possibility of reducing the quantity of spent acid accumulating is to introduce oleum rather than concentrated sulfuric acid as the fresh acid into the process, although oleum is of course more expensive than sulfuric acid.

As an alternative, attempts have been made to recycle the acid. The spent acid accumulating is concentrated by evaporation under normal pressure to an $H_2SO_4$ content of from 95 to 97% (unless otherwise indicated all "%" used herein are "wt.%"). In this super-concentration process, the organic compounds are largely evaporated or destroyed by oxidation, so that a relatively pure acid may be recycled into the process (EP No. 16 987). This process is cost-intensive on account of the high temperatures and the capital investment required for the super-concentration plant.

Another method of improving the economy of the process for producing nitrobenzene is to carry out nitration under adiabatic conditions. Accordingly, the heat of reaction is not dissipated by cooling during the process, but insteadis subsequently used for evaporating the water of reaction so that a sulfuric acid suitable for recirculation is directly obtained. One factor common to all the processes which have been proposed for this purpose (U.S. Pat. No. 3,928,475; U.S. Pat. No. 3,981,935; EP No. 39 556; U.S. Pat. No. 4,021,498; U.S. Pat. No. 4,091,042) is that they require new installations of special corrosion-resistant materials to accommodate the high process temperatures (up to 145° C.) and they also require considerably more stringent safety measures. This offsets the potential advantages of these processes.

The object of the present invention is to improve the production of nitrobenzene by the standard continuous or batch-type isothermal processes such that considerable economic and ecological advantages are obtained over the state-of-the-art.

It has now surprisingly been found that, even when the sulfuric acid is completely recycled for prolonged periods, the need for additional purification may be eliminated without any adverse effect upon the nitrobenzene production process provided that the spent acid accumulating is subjected to medium concentration in vacuo at temperatures of up to at most 195° C.

Accordingly, the present invention provides a process for the production of nitrobenzene by subjecting benzene to isothermal nitration with a mixture of nitric acid and sulfuric acid, separating off the nitrobenzene formed, concentrating the sulfuric acid by evaporation and returning the concentrated sulfuric acid to the benzene nitration stage, characterized in that the sulfuric acid is subjected to medium concentration of from 75 to 92% and preferably to a concentration of from 80 to 90% by evaporation in vacuo at temperatures in the range from 130° to 195° C.

By applying the process according to the invention, therefore, it is possible to carry out concentration by evaporation in vacuo with steam as energy source at temperatures which enable the highly corrosion-resistant materials tantalum, glass, enamelled steel and Teflon to be used. The evaporators used may be, for example, circulation evaporators, falling-film evaporators or thin-layer evaporators. However, horizontal evaporators are particularly suitable for carrying out the concentration process.

In addition to their simple construction and mode of operation, horizontal evaporators have the advantage that, by virtue of the several stages involved, the evaporation of water takes place predominantly at such low sulfuric acid cincentrations that concentration by evaporation to an $H_2SO_4$ content of 92% is even possible without rectification of the vapors, the sulfuric acid losses being at most 1%. At the same time, the bubbles formed by boiling along the heating tubes, which are generally made of tantalum, provide for a very high specific evaporation capacity—a considerable advantage in view of the high cost of the tantalum heat exchangers.

Accordingly, an embodiment of the process according to the invention is particularly preferred wherein concentration by evaporation takes place in one or more horizontal evaporators arranged one behind the other.

The efficiency of the process may be significantly improved by ensuring that concentration takes place in at least three stages through the incorporation of partitions in the horizontal evaporators. Concentration by evaporation in at least five stages is particularly preferred. The vapors from the evaporation process are condensed directly, i.e. without rectification, by direct or indirect cooling.

There is no need for elaborate purification of the recycled acid. It is of particular advantage to heat the dilute acid by means of the concentrated acid. This may be done by passing the cold spent acid through glass or Teflon heat exchangers in countercurrent to the hot, concentrated sulfuric acid and thus heating it to around 100° C.

The process according to the invention is advantageously carried out by evaporating benzene, nitrobenzene and water from the heated, dilute sulfuric acid by evacuation before the dilute sulfuric acid is introduced into the horizontal evaporator. In this way, concentration of the acid by evaporation in the evaporator cannot be impaired. In one particular embodiment of the process according to the invention, the condensed vapors are stripped with steam and benzene and nitrobenzene are returned to the benzene nitration process. Alternatively, the nitro compounds may be extracted with the benzene used for producing the nitrobenzene while the benzene-containing vapor condensate is subjected to an effluent treatment process.

The process according to the invention affords further advantages through its simplicity. It has, surprisingly, been found that the organic compounds do not have to be separated off or destroyed to ensure undisturbed progress of the nitrobenzene production process with complete circulation of the sulfuric acid, nor is there any need for substantial removal of the metal sulfates which enter the sulfuric acid with the nitric acid and through corrosion. According to the invention, the metal sulfates crystallizing from the concentrated acid are removed from the system by periodic flushing of the acid-acid heat exchanger. Accordingly, neither the heat exchange capacity nor the throughflow of acid is adversely affected.

The advantage of using a recycled acid containing dissolved heavy metal sulfates in realtively high concentrations is that the $NO_x$-level is reduced by comparison with the use of fresh acid. In addition, the degree of corrosion in the reaction apparatus is reduced by the relative saturation of the acid with metal sulfates.

According to the present invention, the economy of the process for producing nitrobenzene may be significantly improved by adjusting the concentration of the nitric acid used in the mixture of nitric acid and sulfuric acid to between 60 and 70%. A nitric acid having a concentration of that order is considerably less expensive that the 99% nitric acid normally used. In this way, the cost-intensive extractive nitric acid distillation may be replaced by the evaporation of water from sulfuric acid according to the invention under optimal conditions. The use of 60 to 70% nitric acid affords the additional advantage that the acid contains less $NO_x$ and also less nitrates, particularly aluminum nitrate.

The major advantages of the process according to the invention lie in the fact that the existing installations successfully employed for decades for the isothermal production of nitrobenzene can continue to be used either continuously or in batches. In addition, the sulfuric acid required for the nitration process may be completely recyled.

Evaporation of the water of reaction takes place in vacuo at at most 195° C. so that there are hardly any acid losses and relatively little secondary energy in the form of steam is required.

The use of 60 to 70% nitric acid instead of 98 to 99% nitric acid reduces the quantity of metal salts deposited during concentration of the $H_2SO_4$ by evaporation and also the quantity of $NO_x$ liberated and enables evaporation of the diluting water to be carried out at a low and, hence, energy-favorable concentration level.

Figure 2:
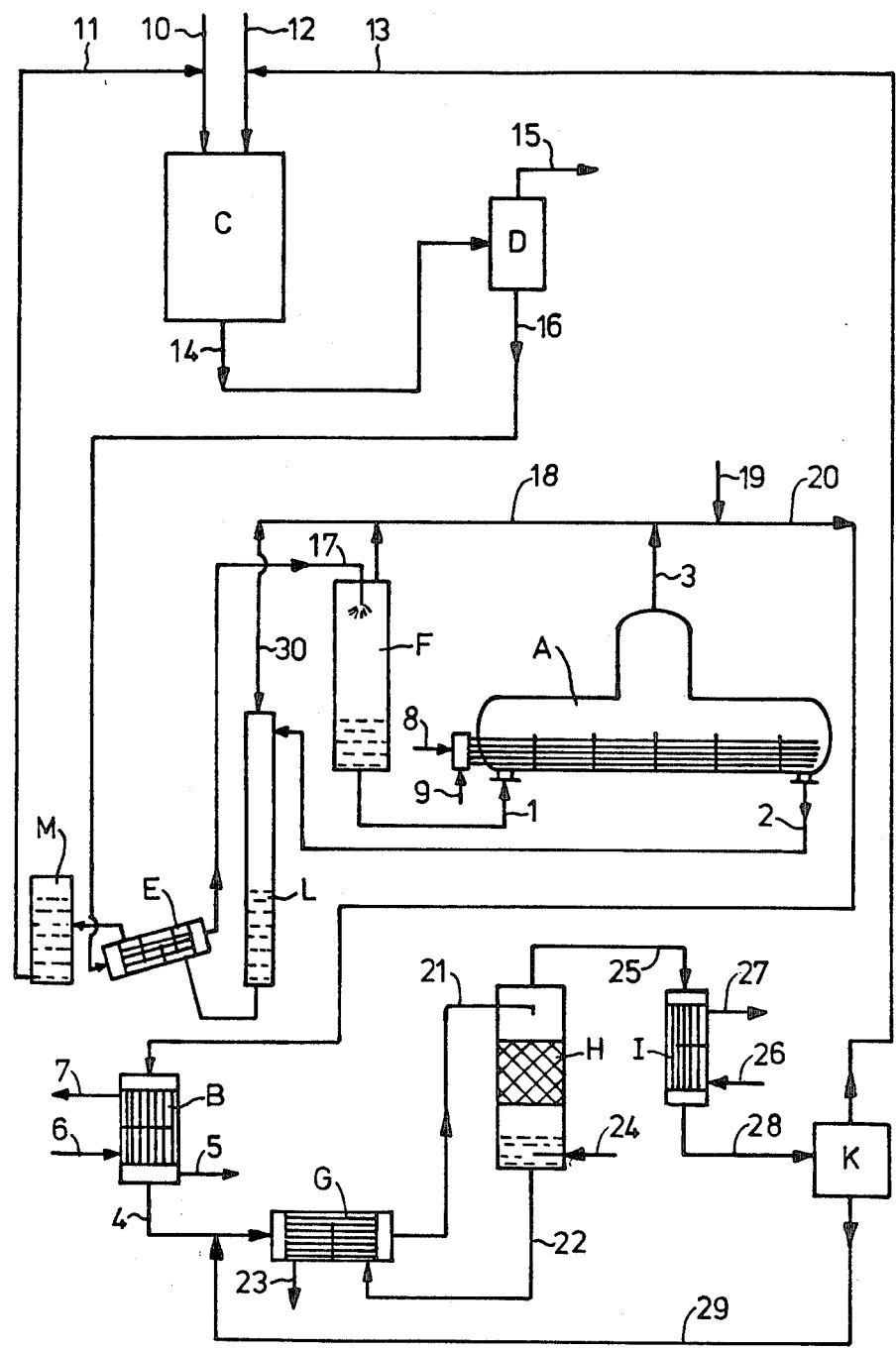

The process according to the invention is described in detail with reference to the accompanying drawings, wherein:

FIG. 1 shows the horizontal evaporator as the preferred apparatus for concentrating the sulfuric acid by evaporation in vacuo; and FIG. 2 shows, by way of example, the combination of the concentration of sulfuric acid by evaporation with the production of nitrobenzene.

With reference to FIG. 1, the horizontal evaporator (A) consists of a horizontal, cylindrical vessel of glass or enamelled steel surmounted by a vapor dome into which a bundle of tantalum tubes is fitted. The steam is introduced (8) and the condensate removed (9) on the same side. Alternatively, it is also possible to install a bundle of tubes in which the steam is introduced on one side and the condensate is removed on the other side. The dilute 65 to 75% sulfuric acid (1) is introduced into the evaporator at one end, preferably from below, and flows axially through the evaporator. The output of the 75 to 92% acid (2) is regulated such that the tantalum tubes are always covered with acid. Between the installed Teflon partitions the acid undergoes intensive mixing under the effect of the bubbles formed on boiling. However, there is always a sudden increase in concentration from one evaporator section to the next. This affords the advantage that significant quantities of sulfuric acid vapor are present in the vapors only at the outlet end of the evaporator and, even then, only if the concentration of the discharged acid (2) is in excess of 90%. The vapors (3) pass from the dome into a condenser (B). The condenser is fed with cooling water (6) which flows off as unpolluted water (7). The vapor condensate (4) is subjected to a further treatment. The non-condensable gases (5) are removed by a vacuum pump. Alternatively, condensation of the vapors may take place by direct contact of the vapors with the vapor condensate circulated through a heat exchanger into the condensor.

The advantageous combination of the production of nitrobenzene with the concentration of sulfuric acid by evaporation is shown in FIG. 2. Nitric acid (10), concentrated recycle sulfuric acid (11), benzene (12) and the benzene-nitrobenzene mixture (13) recovered from the used sulfuric acid (16) are fed into the benzene nitration apparatus (C). When 99% nitric acid (10) is used, a concentration of 80 to 85% is generally sufficient for the sulfuric acid (11). If 60–70% nitric acid (10) is used, it is advisable to concentrate the sulfuric acid by evaporation to 90–93% $H_2SO_4$ so as not to overburden the benzene nitration apparatus (C) with excessive quantities of liquid. Accordingly, the level to which it is desired to concentrate the acid by evaporation is determined by the hydrodynamic load capacity of the benzene nitration plant. The mixture (14) of nitrobenzene and sulfuric acid discharged from the nitration plant is separated in the usual separators (D) into crude nitrobenzene (15) and dilute sulfuric acid (16). It is advisable, although not essential, to remove most of the benzene from the sulfuric acid (16). Similarly destruction of the inorganic nitro compounds by reaction with sulfur dioxide, urea, ammonium sulfate, sulfamic acid or by stripping with steam is possible, but not necessary for the purposes of the invention. The sulfuric acid (16) is introduced into the heat exchanger (E) at a temperature of 30° to 60° C. and leaves it with a temperature of 90° to 120° C. (17). Almost all the benzene and some of the water and nitrobenzene (18) evaporate under reduced pressure in the flash evaporator (F). The substantially benzene-free sulfuric acid (1) is introduced into the horizontal evaporator (A) in which it is concentrated by evaporation to an $H_2SO_4$ concentration of 75–92% at 130°–195° C./10–200 mbars. The hot concentrated acid (2) is used in the heat exchanger (E) to heat the dilute acid (16). The concentrated acid (2) flows into a feed pipe (L) which communicates with the reduced pressure system through a suspended gas pipe (30). The siphon-like feed system ensures a certain acid level in the horizontal evaporator. The acid (2) flows from the feed pipe (L) into the heat exchanger (E). The issuing acid (11) cooled to 50°–70° C. may be cooled with water to 30°–50° C. in another heat exchanger before entering the vessel (M) from which it is fed as required into the benzene nitration apparatus (C). The steam (8) for heating the horizontal evaporator should have a temperature of at most 220° C. to remove any risk of damage to the tantalum by corrosion. The steam condensate (9) may advantageously be used for steam generation. In addition, steam for stripping the vapor condensate may be obtained by flash evaporation. The vapors (3) from the horizontal evaporator (A) are delivered to the condenser (B) together with the vapors (18) from the flash evaporator (F). At the same time, the superheated vapors are cooled to the temperature of saturated steam (20), preferably by spraying in at (19) water or vapor condensate (4). In the condenser (B), the vapors are condensed by indirect cooling with a cooling liquid (6), preferably water. The temperature of the cooling liquid (7) flowing out of the condenser (B) determines the reduced pressure in the evaporation system. The non-condensable gases (5) are removed by a vacuum pump and are subjected to a cleaning process. The vapor condensate (4) is heated (21) by the stripped water (22) in a heat exchanger (G) and introduced into a stripping column (H) in which it is stripped substantially free of benzene and nitrobenzene with steam (24). After cooling (23) by cold vapor condensate (4) in the heat exchanger (G), it flows from the column (H) to the wastewater treatment stage. The steam (25) from the stripping column (H) is condensed by cooling water (26,27) in the heat exchanger (I). The condensate (28) is separated in a separation vessel (K) into an aqueous phase (29), which is returned to the stripping stage, and an organic phase (13) which consists essentially of benzene and nitrobenzene and which is returned to the nitration stage.

Instead of the environmentally favorable, but expensive stripping of the vapor condensate, washing with benzene to remove the nitrobenzene and biological waste water treatment of the benzene-containing effluent are also possible.

The metal sulfates separated from the concentrated acid (2) on cooling are deposited in the heat exchanger (E). This increases the flow resistance and the level of acid in the feed pipe (L). According to the invention, the heat exchanger (E) is emptied when the level of liquid in the feed pipe (L) has substantially reached the level of acid flowing into the pipe. The heat exchanger is cleaned by rinsing with water or dilute acid and the installation is put back into operation.

If large quantities of water are to be evaporated from the dilute sulfuric acid or if concentration by evaporation to 92% $H_2SO_4$ is required, the arrangement of several horizontal evaporators one behind the other affords advantages. The pressure under which evaporation in the individual evaporators takes place should be lower, the higher the concentration of the sulfuric acid discharged.

The advantages of the process according to the invention (Examples 2 and 3) are demonstrated by comparison with a conventional process (Example 1) although the scope of the invention is not limited in any way by the examples.

EXAMPLE 1

(Comparison example)

Spent acid from the nitration of benzene containing 70% of $H_2SO_4$, 0.05% of benzene, 0.03% of nitrobenzene and 0.08% of $NO_x$ was concentrated by evaporation to 96% $H_2SO_4$ in a Pauling-Plinke vessel and recycled to the benzene nitration process. 645 kg/h of concentrated 96% sulfuric acid, 775 kg/h of 99% $HNO_3$ and 1000 kg/h of benzene were used in the benzene nitration process, corresponding to 5% excess of benzene. The 70% spent acid accumulating (872 kg/h) was fed via a heat exchanger heated by the evaporator vapors to the dephlegmator of a Pauling-Plinke evaporator. The vessel of the evaporator was fired by a natural-gas burner. The gas consumption amounted to 64 $m^3_n$/h. The 96% sulfuric acid flowing out of the boiler at a temperature of 330° C. was cooled to 50° C. in a stirrer-equipped cooler and transferred to a storage tank in which metal sulfates were deposited. The acid recycled to the benzene nitration process was colorless.

In addition to steam, the vapors from the head of the dephlegmator column contained 0.44 kg/h of benzene, 0.26 kg/h of nitrobenzene, 0.35 kg/h of $NO_x$ (expressed as $NO_2$) and traces of $SO_2$. After condensation of the vapors, the organic phase was separated off by stripping (cf. Example 2) and returned to the benzene nitration process (0.44 kg/h of benzene and 0.25 kg/h of nitrobenzene). The sulfuric acid losses amounted to 3%.

The energy consumption amounted to 8400 kJ/kg of $H_2O$ evaporated.

EXAMPLE 2

This example relates to one embodiment of the process according to the invention as illustrated in FIG. 2.

4470 kg/h of concentrated (82.5%) sulfuric acid (11) and 2575 kg/h of 99% $HNO_3$ (10) were fed into the benzene nitration apparatus (C). At the same time, 3313 kg/h of benzene (12) and 80 kg/h of a benzene/nitrobenzene mixture (13) containing approximately 33% of benzene were fed in, corresponding to 5% excess of benzene. The mixture discharged (14) was separated into crude nitrobenzene (15) and spent acid (16).

The spent acid (5220 kg/h) containing 70% of $H_2SO_4$ was preheated to 107° C. by the concentrated sulfuric acid (2) in several tube heat exchangers (E) of glass arranged one behind the other. The preheated acid (17) was fed into the flash evaporator (F) in which most of the benzene and nitrobenzene evaporated together with such a quantity of water that 5170 kg/h of acid (1) with a temperature of 100° C. were fed into the horizontal evaporator (A). The bundle of tantalum tubes of the horizontal evaporator was heated with saturated steam at 180° C. (8). The steam consumption amounted to 1300 kg/h, corresponding to 4940 kJ/kg of water evaporated, when the steam condensate (9) was not used. When the steam condensate was used for steam generation, the specific energy demand amounted to 3475 kJ/kg of water evaporated.

The water was evaporated in 5 stages under a pressure of 133 mbars with the temperature rising to 160° C. in the 5th stage. The concentrated acid (2) flowed off through the feed pipe (L) into the heat exchangers (E) in which it was cooled to about 60° C. by means of the spent acid (16). After further cooling to 40° C. in a water-cooled heat exchanger (not shown), the acid (11) was returned from the vessel (M) to the benzene nitration apparatus (C).

200 l/h of vapor condensate (4) were sprayed into the superheated vapors (3) from the horizontal evaporator (A), as a result of which the temperature of the vapors was reduced to 51° C. The condensation of the vapors from the flash evaporator (18) and the horizontal evaporator (3) took place in a water-cooled tube heat exchanger (B). Vapor condensate accumulated at a rate of 790 kg/h (temperature 40° C.). The non-condensable gases (leakage air, 0.6 kg/h of benzene, 0.03 kg/h of nitrobenzene, 0.1 kg/h of $NO_x$) were removed by a water ring pump and delivered to a waste gas combustion furnace.

The vapor condensate contained 2.2 kg of $H_2SO_4$/t, 2.7 kg of benzene/t and 2 kg of nitrobenzene/t of condensate. It was heated to around 90° C. in the heat exchanger (G) and fed into the stripper (H) in which it was stripped by the introduction of 50 kg/h of steam (24) under a pressure of 5 bars into the bottom. The stripped vapor condensate (22) was cooled to 45° C. in the heat exchanger (G) and removed as waste water. The benzene- and nitrobenzene-containing vapor from the stripper (25) was condensed in the condenser (J) and separated in a separation bottle (K) into an organic phase and an aqueous phase. The aqueous phase (29) was combined with the vapor condensate (4) and delivered to the stripper. The organic phase (approx. 2.7 kg/h of benzene and 2 kg/h of nitrobenzene) was returned to the nitration apparatus (C).

After 5-6 months' combined operation, the plant was in a steady state. The acid was colored black-green by iron, chromium, nickel sulfate and other sulfates. Aluminum sulfate and other metal sulfates were continuously deposited in the heat exchanger (E) and had to be removed every 3 to 4 days by regular rinsing with water, for which purpose concentration by evaporation was interrupted for 2 to 3 hours. During the combined operation of the plant, the average $NO_x$-content in the concentrated acid (11) fell from 1000 ppm to 400 ppm. At 0.05% (based on $H_2SO_4$), the losses of $H_2SO_4$ during concentration by evaporation were very low. No adverse effects attributable to recycling of the sulfuric acid were observed during the benzene nitration process.

EXAMPLE 3

The benzene nitration process and concentration of the sulfuric acid by evaporation were carried out in the same way as described in Example 2 with the following differences:

67% $HNO_3$ was used as the nitric acid (10). The sulfuric acid was concentrated by evaporation from 70 to 92% $H_2SO_4$. Two evaporators (A) heated with saturated steam (8) at 195° C. were connected in parallel for evaporation. The pressure in the evaporators amounted to 40 mbars and the temperature of the acid flowing off (2) to 182° C.

3500 kg/h of waste acid (16) containing 70% of $H_2SO_4$, 0.05% of benzene, 0.03% of nitrobenzene and 0.01% of $NO_2$ were fed into the flash evaporator (F) after preheating to 110° C. A total of 2640 kg/h of 92% sulfuric acid (2) with a temperature of 182° C. flowed off from the horizontal evaporators (A). The vapors were worked up in the same way as described in Example 2. After a steady state had been established, the heat exchanger (E) had to be rinsed every 15 to 20 days. The $NO_x$-content of the concentrated acid (11) amounted to 0.006%. The waste gas contained approx. 1 g of $NO_x$/h.

It will be understood that the specification and examples are illustrative but not limitative of the present invention and that other embodiments within the spirit and scope of the invention will suggest themselves to those skilled in the art.

We claim:

1. In the production of nitrobenzene by subjecting an excess of benzene to isothermal nitration with a mixture of nitric acid and sulfuric acid, separating off the nitrobenzene formed, concentrating spent acid consisting essentially of sulfuric acid and a small amount of impurities by evaporation and returning the concentrated sulfuric acid to the benzene nitration stage, the improvement which comprises concentrating sulfuric acid to a concentration of 75 to 92 wt. % by evaporation in vacuo at temperatures in the range from 130° to 195° C. in a plurality of horizontal stages of increasing concentration, the vapors from the evaporation being condensed without rectification, whereby the flow through the horizontal stages results in improved NOx decontamination.

2. A process according to claim 1, wherein evaporation takes place in at least 3 stages.

3. A process according to claim 2, wherein evaporation takes place in at least 5 stages.

4. A process according to claim 1, wherein the evaporation vapors are directly cooled without rectification.

5. A process according to claim 1, wherein the sulfuric acid to be 75 to 92 wt.% concentrated is preheated in a heat exchanger by the concentrated acid.

6. A process according to claim 1, wherein before the hot dilute sulfuric acid to be concentrated is introduced into the horizontal stages it is evacuated thereby to evaporate therefrom benzene, nitrobenzene and water.

7. A process according to claim 6, wherein evaporated vapors of benzene, nitrobenzene and water are condensed and then stripped with steam, the stripped benzene and nitrobenzene being returned to the benzene nitration process.

8. A process according to claim 5, including the further step of periodically rinsing the preheating heat exchanger with water thereby to remove metal sulfates which have crystallized from the concentrated acid.

9. A process according to claim 1, wherein the concentration of the nitric acid in the nitric acid/sulfuric acid mixture amounts to between 60 to 70 wt.%.

10. A process according to claim 1, wherein concentration takes place in at least two horizontal stages arranged in series.

11. A process according to claim 1, wherein the sulfuric acid is concentrated to a concentration of from 80 to 90 wt.%.

12. A process according to claim 1, wherein the sulfuric acid is concentrated at a pressure of 10 to 200 mbars.

13. A process according to claim 1, wherein steam of at most 220° C. is used for heating in the horizontal stages.

14. A process according to claim 5, wherein the sulfuric acid to be concentrated is 65 to 75 wt. % sulfuric acid.

15. A process according to claim 1, wherein the plurality of horizontal stages comprise at least one horizontal evaporator, said evaporator comprising a horizontal, cylindrical vessel surmonted by a vapor dome, said evaporator further comprising a bundle of tubes, vapors exit the evaporator through the dome, said sulfuric acid entering the evaporator at one end, from below, and flow axially through the evaporator and exit out of the other end of the evaporator.

16. A process according to claim 15, wherein the tubes are tantalum tubes.

* * * * *